United States Patent
Choudary et al.

(10) Patent No.: US 6,215,024 B1
(45) Date of Patent: Apr. 10, 2001

(54) PROCESS FOR THE PRODUCTION OF AMIDES FROM AMINES

(75) Inventors: Boyapati Manoranjan Choudary; Veldurthy Bhaskar; Mannepalli Lakshmi Kantam; Kottapalli Koteswara Rao; Kondapuram Vijaya Raghavan, all of Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/411,971

(22) Filed: Oct. 4, 1999

(30) Foreign Application Priority Data

Sep. 16, 1999 (IN) .............................. 1239/DEL/99

(51) Int. Cl.$^7$ ................................. C07C 231/02
(52) U.S. Cl. ......................... 564/138; 564/141; 549/480; 546/308
(58) Field of Search ..................... 564/161, 123, 564/166, 182, 138, 172, 141, 192, 139, 204, 191, 216; 546/304; 549/480

(56) References Cited

PUBLICATIONS

CA:100: 191037 abs of Huaxue Shijie by Zhao 24(9) pp. 271–275, 1983.*
CA:128:140459 abs of JP10025264, Jan. 1998.*
CA:127:205165 abs of Chem Commun by Li et al 15 pp. 1389–1390, 1997.*
CA:84:74034 abs of J Chromatogr by Schindlbauer et al 115 (2) pp. 311–317, 1975.*
CA:104:224717 abs of CS223945, Nov. 1983.*
CA:118:168726 abs of Sntyh Commun by Villemin et al 22(22) pp. 3181–3187, 1992.*
Verlag, G.T. "Houben–Weyl, Methoden Der Organischem Chemie." vol. E5, (1985) pp. 941–966 (XP002130119).
Chemical Abstracts, vol. 128, No. 15 (1998) of Wali, A. et al. "Montmorillonite clay catalysis . . . " p. 545, column 1 (XP 002130120).

* cited by examiner

Primary Examiner—Jean F. Vollano
(74) Attorney, Agent, or Firm—Ladas and Parry

(57) ABSTRACT

The present invention provides a novel single step process for the production of amides from amines comprising reaction of amines with an acylating agent comprising of a carboxylic acid in a molar ratio of 1:3 to 1:10 in the presence of reusable natural montmorillonite/metal ion-exchanged clay catalysts, in a suitable solvent medium at a temperature in the range of 30–160° C. for a period of 0.02 to 6 hrs, and recovering the corresponding amides by a conventional simple work-up procedure.

9 Claims, No Drawings

PROCESS FOR THE PRODUCTION OF AMIDES FROM AMINES

FIELD OF THE INVENTION

The present invention relates to novel process for the production of amides from amines using carboxylic acids as the acylating agents and natural/modified montmorillonite clays as catalysts.

This invention particularly relates to an ecofriendly process for the production of amides from aromatic, aliphatic, cyclic, acyclic and heterocyclic amines having carbon atoms in the range of $C_1$ to $C_{20}$ using carboxylic acids as the acylating agents and montmorillonite clays as catalysts and dispensing with the use of expensive corresponding anhydride as a reagent and corrosive, toxic sulfuric acid, hydrochloric acid, sulfonic acids as catalysts. This process totally eliminates the disposal of salts formed consequent to the neutralisation of $H_2SO_4$ or sulfonic acids and the use of expensive anhydrides.

BACKGROUND OF THE INVENTION

These amides belong to a very important class of chemicals having applications as intermediates for pharmaceuticals, azo and sulfur dyes, fine chemicals, drugs, as stabilizers for hydrogen peroxide, as photographic chemicals and as antioxidants. N-acetyl p-amino phenol (APAP), commonly known as acetaminophen or paracetamol, is known for a wide variety of uses. Its medicinal use is very well known, notably as a non-prescription analgesic and anti-pyretic agent with properties similar to aspirin. It is also a major component in over 200 other drug formulations.

Amide formation is generally performed with acyl chlorides or anhydrides in presence of bases, 4-dimethylaminopyridine, 4-pyrrolidinopyridine, trimethylamine etc. Lewis acids such as zinc chloride, cobalt chloride, scandium trifluoromethanesulphonate which are good in the acetylation of amines with acetic anhydride generates one molecule of carboxylic acid for every molecule of anhydride consumed and therefore renders the process very expensive. To optimise the yields of ester/amide formation 2–15 molar equivalents of condensing agents such as sulfuric acid, tosylchloride, trifluoroacetic anhydride, polyphosphate ester, N, $N_1$-dicyclohexylcarbodiimide, graphite etc., are generally employed. Heterogeneous acidic and superacid catalysts have proved to be useful in some reactions because of their activity, selectivity, reusability, non-corrosivity and virtual absence of effluent treatment which usually is associated with the homogeneous catalysts.

U.S. Pat. No. 2,462,221 Feb. 22, 1949 describes a process wherein acetanilide is prepared by heating aniline with 20% excess of acetic acid in the presence of 2–5% by wt of benzene. The reaction mixture was heated in the range of 130–200° C. Toluidine is acetylated in similar way to get very good yields. U.S. Pat. No. 2,551,047 May 1, 1951 describes a process wherein N-aryl acetamides are prepared by heating an arylamine with up to 25% excess of acetic acid in presence of up to 5% of AcOR, which acts as entrainer of water. The reaction temperatures are in the range of 130–200° C. and the reaction time is 21 hrs for acetanilide preparation. The drawbacks in the above-described processes are that reactions are of quite long duration and the reaction temperatures used are very high. U.S. Pat. No. 4,288,592 Sep. 8, 1981 describes a process wherein the amides are prepared by reacting amines with acid halides or anhydrides in an inert organic diluent, in the presence of molecular sieves. The drawbacks in the above-described processes are that acid halides or anhydrides are used as acylating agents and all the reactions are performed in nitrogen atmosphere.

A communication in J. Chem. Soc., Chem. Commun., 1987,114 discloses the acetylation of amines in presence of acetic anhydride as the acetylating agent and cobalt(II) chloride as catalyst. The drawbacks in the above process are in the use of expensive acetic anhydride.

A communication in J. Chem. Soc., Chem. Commun., 1997,1389, discloses the use of montmorillonite K-10 and KSF catalysts for the acetylation of primary and secondary amines in presence of acetic anhydride the acetylating agent and finds that the results are remarkable. The drawbacks in the above process are the use of an expensive acetic anhydride as acetylating agent. Also, the reactions are not selective i. e., both the functional groups are acetylated in the case of 2-aminophenol, depending upon the molar ratios of the substrate and the acetic anhydride used. Moderate yields are obtained in this process.

In almost all the U.S. Pat. Nos. 4,264,526; 4,264,525; 4,565,890; 3,076,030; 3,341,587 and 5,155,269, the acetylation of p-amino phenol was performed in presence of acetic anhydride/acetic anhydride in aqueous solvent system. U.S. Pat. No. 4,264,526, Apr. 28, 1981 describes a process for the production of aminophenols and N-acetyl p-aminophenol (APAP) comprising alkaline hydrolysis of halonitrobenzene to nitrophenol and from nitrophenols to aminophenols using a borate ion additive during hydrogenation to eliminate undesirable by-products and colour formation. CS Patent 223,945 (Cl. C07C 91/44) Nov. 15, 1985 discloses a process wherein the acetylation of aminophenols with acetic anhydride in ethyl acetate or AcOH gives moderate yields of acetaminophen. The drawbacks in the above processes are the use of acetic anhydride as acetylating agent and the yields are moderate.

U.S. Pat. No. 4,670,589, Jun. 2, 1987 describes a process for the production of APAP by hydrogenation of p-nitrophenol to p-amino phenol (PAP), and concurrently acetylating the PAP with acetic anhydride. U.S. Pat. No. 5,648,535, Jul. 15, 1997, describes a process for the production of N-acylaminophenols by the concurrent hydrogenation of a nitrophenol to an aminophenol and the acylation of the aminophenol with acyl anhydride on a continuous basis in a stirred tank reactor. The drawbacks in the above processes are the use of excess acetic anhydride as acetylating agent/solvent system, difficulty of mono-acetylating the amino group, longer reaction times, oligomerization of the hydroxyl aromatic amine, and color body formation.

Obviously different approaches have been employed both on laboratory and commercial scale to prepare the industrially useful amides, and the traditional homogeneous catalysed reactions are being less favoured owing to the problems of separation and reuse. The present trend is to develop solid acids from cheaply available sources, and especially of clays.

OBJECTS OF THE INVENTION

The main object of the present invention is to provide a novel process for the production of amides from amines, which obviates the drawbacks as detailed above.

Another object of the invention is to provide a process wherein the use of expensive reactants such as anhydrides is obviated.

It is yet another object of the invention to provide a process for the production of amides from amines wherein the formation of excessive effluents is avoided.

Still another object of the present invention is the usage of non-corrosive and cheaply available heterogeneous solid acid catalysts for the first time for easy adaptability in a continuous process.

Still another object of the present invention is to provide a process for the production of amides from amines wherein at least some of the reactants can be recovered by distillation and reused.

It is another object of the invention to provide a process for the formation of amides from amines wherein maximum yields of amides are obtained.

Still another object of the present invention is to provide the process wherein a wider range of amines as starting material can be utilised.

Still another object of the present invention is to provide a process for the production of amides from amines wherein the reaction takes place at lower temperatures.

Yet another object of the present invention is to accomplish the process in short time and in an inexpensive manner.

SUMMARY OF THE INVENTION

These and the other objects of the present invention are achieved by the process of the present invention for the production of amides from amines using a carboxylic acid selected from the group consisting of acetic acid, propionic acid, butyric acid etc., as acylating agents and natural/modified montmorillonite clays as catalysts, Accordingly the present invention provides a novel single step process for the production of amides from amines which comprises reacting an amine having 1–20 carbon atoms and selected from the group comprising aromatic, aliphatic, cyclic and heterocyclic amines with an acylating agent comprising of a carboxylic acid such as herein described in a molar ratio of 1:3 to 1:10 in the presence of reusable natural montmorillonite/metal ion-exchanged clay catalysts, in a suitable solvent medium at a temperature in the range of 30–160° C. for a period of 0.02 to 6 hrs, and recovering the corresponding amides by a conventional simple work-up procedure.

In an embodiment of the present invention the clay catalyst used is metal-ion exchanged montmorillonite/natural montmorillonite clay.

In another embodiment of the present invention the metal ions used are as $Fe^{3+}$, $Co^{2+}$, $Cu^{2+}$, $Zn^{2+}$, $Al^{3+}$, $Ce^{3+}$, $La^{3+}$ or $Zr^{4+}$-montmorillonites.

In another embodiment of the present invention, solvents used for the reaction are selected from aromatic hydrocarbons such as dichloroethane, acetic acid, chlorobenzene and toluene.

In yet another embodiment of the present invention acetic acid, propionic acid, butyric acid etc., are used as acylating agents for the first time instead of expensive corresponding anhydrides for the preparation of amides, the amount used ranging from 3 to 10 mmols/mmole of substrate.

In another embodiment of the invention the starting amines used for the production of amides are selected from aromatic, aliphatic, cyclic and heterocyclic amines.

In still another embodiment of the present invention amines with 1–20 carbon atoms used for the first time were selected from aromatic, aliphatic, cyclic and heterocyclic amines such as p-aminophenol; o-aminophenol; p-nitroaniline; m-nitroaniline; p-chloroaniline; aniline (aminobenzene); benzylamine; phenylethylamine; p-anisidine; (D)-(+)-α-methylbenzylamine; 4-bromo-2-methylaniline; 4-amino-2-nitrotoluene; 2-(2-amino ethyl) pyridine; furfurylamine; 2-methyl-2-amino-1,3-propanediol; dodecylamine; propargyl amine; cyclohexylamine and 1-naphthylamine.

In still another embodiment of the present invention recovery of the amides is carried out by separating the catalyst through filtration and removing the solvent by rotavapor/distillation.

In still another embodiment of the present invention the carboxylic acids are recovered by distillation and reused.

The present invention also relates to an improved process for the production of amides from amines using acetic acid, propionic acid, butyric acid etc., as acylating agents and clays/modified montmorillonite clays as catalysts in solvent/without solvent medium at 30° C. to 160° C. for a period of 0.02 to 6 hrs, and recovery of the corresponding amides by easy work-up.

In the present invention, abundantly available montmorillonite sourced from nature is used as the solid acid catalyst for the acylation of various amines with acetic acid, propionic acid, butyric acid etc., as acylating agents without any further purification (example 1b) for the first time. The activity of the natural montmorillonite is comparable with metal ion exchanged K10 montmorillonite clay catalysts (with slight change in activity/reaction time) in the selective acylation of amines. While K10 montmorillonite as supplied from Fluka will lead to many side products such as di-acetylation and oligomerization or polymerised products, and alkylation on the aromatic solvents used in the reaction. These results indicate that right admix of Bronsted and Lewis acidities is an essential requirement to trigger catalytic acylations of amines with carboxylic acid to afford optimum yields. Natural montmorillonite sourced from nature has Lewis acid sites resulted from the transition metal sites exchanged on montmorillonite and Bronsted acid sites. In the acid treated montmorillonite, K10, the density of the Bronsted acidic sites increases because of increased number of broken edges resulted from broken layers, while the Lewis acidity decreases due to desorption of exchanged metal ion on montmorillonite inherently present in natural montmorillonite during acid treatment. K10 montmorillonite with very high Bronsted acidity thus induces the side product formation as exemplified above. Introduction of metal through ion exchange process to montmorillonite K10 increases the Lewis acidity and simultaneously decreases Bronsted acidity to form right admix of Bronsted and Lewis acid sites to effect acylation of amines selectively.

The present invention will now be described in greater detail with reference to the following illustrative but non-limitative examples.

All the metal ion-exchanged montmorillonite clay catalysts were prepared as described in example 1 and employed in the N-acylation of amines with carboxylic acids as acylating agents as described in examples 2 to 37.

EXAMPLE 1

Catalyst Preparation a) $Fe^{3+}$-exchanged montmorillonite: 80 g of K10-montmorillonite (obtained from M/S Fluka, a Sigma Aldrich company—Switzerland) was added to a 1 lt. aqueous solution of $FeCl_3$(1.0 M) under stirring. Stirring was maintained for 16–30 hrs in order to saturate the exchange capacity of K10 montmorillonite. The clay suspension was centrifuged and the supernatant solution was discarded. Washing cycles were repeated until disappearance of $Cl^-$ ions from the discarded water. The clay was dried overnight in an oven at 120° C. and finely ground in a mortar.

Metal ion-exchanged clays such as $Fe^{3+}$, $Co^{2+}$, $Cu^{2+}$, $Zn^{2+}$, $Al^{3+}$, $Ce^{3+}$, $La^{3+}$ or $Zr^{4+}$-montmorillonites catalysts were prepared in a similar procedure by dissolving the corresponding metal salts.

b) Natural montmorillonite: The clay (natural montmorillonite, obtained from M/S Neelakanth chemical works, Jodhpur, India) was dried at 120° C. for 24 hrs and used.

EXAMPLE 2

Aniline (5 mmol, 0.465 g) and glacial acetic acid (50 mmol, 3 g) were heated at reflux temperature 116° C. in a two-necked round bottom flask (50 ml) in presence of $Fe^{3+}$-montmorillonite clay (0.1 g) catalyst. After completion of the reaction (followed by TLC), the reaction mixture was filtered and the filtrate was concentrated on rotavapor/distilled to get the pure product (0.66 g).

EXAMPLE 3

Aniline (5 mmol, 0.465 g) and glacial acetic acid (50 mmol, 3 g) were heated at reflux temperature 116° C. in a two-necked round bottom flask (50 ml) in presence of natural montmorillonite clay (0.1 g) catalyst. After completion of the reaction (followed by TLC), the reaction mixture was filtered and the filtrate was concentrated on rotavapor/distilled to get the pure product (0.66 g).

EXAMPLE 4 p-nitroaniline (5 mmol, 0.69) and glacial acetic acid (50 mmol, 3 g) were heated at reflux temperature 116° C. in a two-necked round bottom flask (50 ml) in presence of natural montmorillonite clay (0.1 g) catalyst. After completion of the reaction (followed by TLC), the reaction mixture was filtered and the filtrate was concentrated on rotavapor/distilled to get the pure product (0.87 g).

EXAMPLE 5 m-nitroaniline (5 mmol, 0.69 g) and glacial acetic acid (50 mmol, 3 g) were heated at reflux temperature 116° C. in a two-necked round bottom flask (50 ml) in presence of natural montmorillonite clay (0.1 g) catalyst. After completion of the reaction (followed by TLC), the reaction mixture was filtered and the filtrate was concentrated on rotavapor/distilled to get the pure product (0.87 g).

EXAMPLE 6 p-chloroaniline (5 mmol, 0.637 g) and glacial acetic acid (50 mmol, 3 g) were heated at reflux temperature 116° C. in a two-necked round bottom flask (50 ml) in presence of $Fe^{3+}$-montmorillonite clay (0.1 g) catalyst. After completion of the reaction (followed by TLC), the reaction mixture was filtered and the filtrate was concentrated on rotavapor/distilled to get the pure product (0.83 g).

EXAMPLE 7 p-chloroaniline (5 mmol, 0.637 g) and glacial acetic acid (50 mmol, 3 g) were heated at reflux temperature 116° C. in a two-necked round bottom flask (50 ml) in presence of natural montmorillonite clay (0.1 g) catalyst. After completion of the reaction (followed by TLC), the reaction mixture was filtered and the filtrate was concentrated on rotavapor/distilled to get the pure product (0.83 g).

EXAMPLE 8 p-anisidine (5 mmol, 0.615 g) and glacial acetic acid (50 mmol, 3 g) were heated at reflux temperature 116° C. in a two-necked round bottom flask (50 ml) in presence of $Fe^{3+}$-montmorillonite clay (0.1 g) catalyst. After completion of the reaction (followed by TLC), the reaction mixture was filtered and the filtrate was concentrated on rotavapor/distilled to get the pure product (0.82 g).

EXAMPLE 9 p-anisidine (5 mmol, 0.615 g) and glacial acetic acid (50 mmol, 3 g) were heated at reflux temperature 116° C. in a two-necked round bottom flask (50 ml) in presence of natural montmorillonite clay (0.1 g) catalyst. After completion of the reaction (followed by TLC), the reaction mixture was filtered and the filtrate was concentrated on rotavapor/distilled to get the pure product (0.82 g).

EXAMPLE 10 p-aminophenol (5 mmol, 0.545 g) and glacial acetic acid (50 mmol, 3 g) were heated at reflux temperature 116° C. in a two-necked round bottom flask (50 ml) in presence of $Fe^{3+}$-montmorillonite clay (0.1 g) catalyst. After completion of the reaction (followed by TLC), the reaction mixture was filtered and the filtrate was concentrated on rotavapor/distilled to get the pure product (0. 74 g).

EXAMPLE 11 p-aminophenol (5 mmol, 0.545 g) and glacial acetic acid (50 mmol, 3 g) were heated at reflux temperature 116° C. in a two-necked round bottom flask (50 ml) in presence of natural montmorillonite clay (0.1 g) catalyst. After completion of the reaction (followed by TLC), the reaction mixture was filtered and the filtrate was concentrated on rotavapor/distilled to get the pure product (0.74 g).

EXAMPLE 12 o-aminophenol (5 mmol, 0.545 g) and glacial acetic acid (50 mmol, 3 g) were heated at reflux temperature 116° C. in a two-necked round bottom flask (50 ml) in presence of $Fe^{3+}$-montmorillonite clay (0.1 g) catalyst. After completion of the reaction (followed by TLC), the reaction mixture was filtered and the filtrate was concentrated on rotavapor/distilled to get the pure product (0.74 g).

EXAMPLE 13 o-amino phenol (5 mmol, 0.545 g) and glacial acetic acid (50 mmol, 3 g) were heated at reflux temperature 116° C. in a two-necked round bottom flask (50 ml) in presence of natural montmorillonite clay (0.1 g) catalyst. After completion of the reaction (followed by TLC), the reaction mixture was filtered and the filtrate was concentrated on rotavapor/distilled to get the pure product (0.74 g).

EXAMPLE 14

4-bromo-2-methyl aniline (5 mmol, 0.93 g) and glacial acetic acid (50 mmol, 3 g) were heated at reflux temperature 116° C. in a two-necked round bottom flask (50 ml) in presence of $Fe^{3+}$-montmorillonite clay (0.1 g) catalyst. After completion of the reaction (followed by TLC), the reaction mixture was filtered and the filtrate was concentrated on rotavapor/distilled to get the pure product (1.10 g).

EXAMPLE 15

4-bromo-2-methyl aniline (5 mmol, 0.93 g) and glacial acetic acid (50 mmol, 3 g) were heated at reflux temperature 116° C. in a two-necked round bottom flask (50 ml) in presence of natural montmorillonite clay (0.1 g) catalyst. After completion of the reaction (followed by TLC), the reaction mixture was filtered and the filtrate was concentrated on rotavapor/distilled to get the pure product (1.11 g).

EXAMPLE 16

4-amino-2-nitrotoluene (5 mmol, 0.76 g) and glacial acetic acid (50 mmol, 3 g) were heated at reflux temperature 116° C. in a two necked round bottom flask (50 ml) in presence of $Fe^{3+}$-montmorillonite clay (0.1 g) catalyst. After completion of the reaction (followed by TLC), the reaction mixture was filtered and the filtrate was concentrated on rotavapor/distilled to get the pure product (0.95 g).

EXAMPLE 17

4-amino-2-nitrotoluene (5 mmol, 0.76 g) and glacial acetic acid (50 mmol, 3 g) were heated at reflux temperature 116° C. in a two necked round bottom flask (50 ml) in presence of natural montmorillonite clay (0.1 g) catalyst. After completion of the reaction (followed by TLC), the reaction mixture was filtered and the filtrate was concentrated on rotavapor/distilled to get the pure product (0.95 g).

EXAMPLE 18

Benzylamine (5 mmol, 0.535 g) and glacial acetic acid (50 mmol, 3 g) were heated at reflux temperature 116° C. in a two-necked round bottom flask (50 ml) in presence of $Fe^{3+}$-montmorillonite clay (0.1 g) catalyst. After completion of the reaction (followed by TLC), the reaction mixture was filtered and the filtrate was concentrated on rotavapor/distilled to get the pure product (0.73 g).

EXAMPLE 19

Benzylamine (5 mmol, 0.535 g) and glacial acetic acid (50 mmol, 3 g) were heated at reflux temperature 116° C. in a two-necked round bottom flask (50 ml) in presence of natural montmorillonite clay (0.1 g) catalyst. After completion of the reaction (followed by TLC), the reaction mixture was filtered and the filtrate was concentrated on rotavapor/distilled to get the pure product (0.73 g).

EXAMPLE 20

Phenethylamine (5 mmol, 0.60 g) and glacial acetic acid (50 mmol, 3 g) were heated at reflux temperature 116° C. in a two-necked round bottom flask (50 ml) in presence of natural montmorillonite clay (0.1 g) catalyst. After completion of the reaction (followed by TLC), the reaction mixture was filtered and the filtrate was concentrated on rotavapor/distilled to get the pure product (0.80 g), without any racemization and was found to be optically pure.

EXAMPLE 21

(D)-(+)-α-methyl benzylamine (5 mmol, 0.60 g) and glacial acetic acid (50 mmol, 3 g) were heated at reflux temperature 116° C. in a two necked round bottom flask (50 ml) in presence of $Fe^{3+}$-montmorillonite clay (0.1 g) catalyst. After completion of the reaction (followed by TLC), the reaction mixture was filtered and the filtrate was concentrated on rotavapor/distilled to get the pure product (0.79 g), without any racemization and was found to be optically pure.

EXAMPLE 22

(D)-(+)-α-methyl benzylamine (5 mmol, 0.60 g) and glacial acetic acid (50 mmol, 3 g) were heated at reflux temperature 116° C. in a two necked round bottom flask (50 ml) in presence of natural montmorillonite clay (0.1 g) catalyst. After completion of the reaction (followed by TLC), the reaction mixture was filtered and the filtrate was concentrated on rotavapor/distilled to get the pure product (0.80 g).

EXAMPLE 23

Furfurylamine (5 mmol, 0.485 g) and glacial acetic acid (50 mmol, 3 g) were heated at reflux temperature 116° C. in a two-necked round bottom flask (50 ml) in presence of $Fe^{3+}$-montmorillonite clay (0.1 g) catalyst. After completion of the reaction (followed by TLC), the reaction mixture was filtered and the filtrate was concentrated on rotavapor/distilled to get the pure product (0.67 g).

EXAMPLE 24

Furfurylamine (5 mmol, 0.485 g) and glacial acetic acid (50 mmol, 3 g) were heated at reflux temperature 116° C. in a two-necked round bottom flask (50 ml) in presence of natural montmorillonite clay (0.1 g) catalyst. After completion of the reaction (followed by TLC), the reaction mixture was filtered and the filtrate was concentrated on rotavapor/distilled to get the pure product (0.67 g).

EXAMPLE 25

2-(2-amino ethyl)pyridine (5 mmol, 0.61 g) and glacial acetic acid (50 mmol, 3 g) were heated at reflux temperature 116° C. in a two-necked round bottom flask (50 ml) in presence of $Fe^{3+}$-montmorillonite clay (0.1 g) catalyst. After completion of the reaction (followed by TLC), the reaction mixture was filtered and the filtrate was concentrated on rotavapor/distilled to get the pure product (0.78 g).

EXAMPLE 26

2-(2-amino ethyl)pyridine (5 mmol, 0.61 g) and glacial acetic acid (50 mmol, 3 g) were heated at reflux temperature 116° C. in a two-necked round bottom flask (50 ml) in presence of natural montmorillonite clay (0.1 g) catalyst. After completion of the reaction (followed by TLC), the reaction mixture was filtered and the filtrate was concentrated on rotavapor/distilled to get the pure product (0.78 g).

EXAMPLE 27

Cyclohexylamine (5 mmol, 0.495 g) and glacial acetic acid (50 mmol, 3 g) were heated at reflux temperature 116° C. in a two-necked round bottom flask (50 ml) in presence of $Fe^{3+}$-montmorillonite clay (0.1 g) catalyst. After completion of the reaction (followed by TLC), the reaction mixture was filtered and the filtrate was concentrated on rotavapor/distilled to get the pure product (0.68 g).

EXAMPLE 28

Cyclohexylamine (5 mmol, 0.495 g) and glacial acetic acid (50 mmol, 3 g) were heated at reflux temperature 116° C. in a two-necked round bottom flask (50 ml) in presence of natural montmorillonite clay (0.1 g) catalyst. After completion of the reaction (followed by TLC), the reaction mixture was filtered and the filtrate was concentrated on rotavapor/distilled to get the pure product (0.68 g).

EXAMPLE 29

Propargylamine (5 mmol, 0.275 g) and glacial acetic acid (5 mmol, 3 g) were heated at reflux temperature 116° C. in a two-necked round bottom flask (50 ml) in presence of Fe³1-montmorillonite clay (0.1 g) catalyst. After completion of the reaction (followed by TLC), the reaction mixture was filtered and the filtrate was concentrated on rotavapor/distilled to get the pure product (0.35 g).

EXAMPLE 30

Propargylamine (5 mmol, 0.275 g) and glacial acetic acid (50 mmol, 3 g) were heated at reflux temperature 116° C. in a two-necked round bottom flask (50 ml) in presence of natural montmorillonite clay (0.1 g) catalyst. After completion of the reaction (followed by TLC), the reaction mixture was filtered and the filtrate was concentrated on rotavapor/distilled to get the pure product (0.34 g).

EXAMPLE 31

Dodecylamine (5 mmol, 0.93 g) and glacial acetic acid (50 mmol, 3 g) were heated at reflux temperature 116° C. in a two-necked round bottom flask (50 ml) in presence of $Fe^{3+}$-montmorillonite clay (0.1 g) catalyst. After completion of the reaction (followed by TLC), the reaction mixture was filtered and the filtrate was concentrated on rotavapor/distilled to get the pure product (1.1 g).

EXAMPLE 32

Dodecylamine (5 mmol, 0.93 g) and glacial acetic acid (50 mmol, 3 g) were heated at reflux temperature 116° C. in a two-necked round bottom flask (50 ml) in presence of natural montmorillonite clay (0.1 g) catalyst. After completion of the reaction (followed by TLC), the reaction mixture was filtered and the filtrate was concentrated on rotavapor/distilled to get the pure product (1.1 g).

EXAMPLE 33

2-methyl-2-amino-1,3-propanediol (5 mmol, 0.525 g) and glacial acetic acid (5 mmol, 3 g) were heated at reflux temperature 116° C. in a two necked round bottom flask (50 ml) in presence of natural montmorillonite clay (0.1 g) catalyst. After completion of the reaction (followed by TLC), the reaction mixture was filtered and the filtrate was concentrated on rotavapor/distilled to get the pure product (1.1 g).

EXAMPLE 34

1-Naphthylamine (5 mmol, 0.715 g) and glacial acetic acid (50 mmol, 3 g) were heated at reflux temperature 116° C. in a two necked round bottom flask (50 ml) in presence of $Fe^{3+}$-montmorillonite clay (0.1 g) catalyst. After completion of the reaction (followed by TLC), the reaction mixture was filtered and the filtrate was concentrated on rotavapor/distilled to get the pure product (0.92 g).

EXAMPLE 35

1-Naphthylamine (5 mmol, 0.715 g) and glacial acetic acid (50 mmol, 3 g) were heated at reflux temperature 116° C. in a two necked round bottom flask (50 ml) in presence of natural montmorillonite clay (0.1 g) catalyst. After completion of the reaction (followed by TLC), the reaction mixture was filtered and the filtrate was concentrated on rotavapor/distilled to get the pure product (0.92 g).

EXAMPLE 36

(D)-(+)-αmethyl benzylamine (5 mmol, 0.06 g) and propionic acid (50 mmol, 3.7 g) were heated at reflux temperature 142° C. in a two necked round bottom flask (50 ml) in presence of $Fe^{3+}$-montmorillonite clay (0.1 g) catalyst. After completion of the reaction (followed by TLC), the reaction mixture was filtered and the filtrate was distilled to get the pure product (0.87 g), without any racemization and was found to be optically pure.

EXAMPLE 37

(D)-(+)-αmethyl benzylamine (5 mmol, 0.06 g) and propionic acid (50 mmol, 3.7 g) were heated at reflux temperature 142° C. in a two necked round bottom flask (50 ml) in presence of natural montmorillonite clay (0.1 g) catalyst. After completion of the reaction (followed by TLC), the reaction mixture was filtered and the filtrate was distilled to get the pure product (0.87 g), without any racemization and was found to be optically pure

TABLE 1

N-acetylation of amines using acetic acid as acetylating agent

| S. No. | Example | Amine[a] (Substrate) | Catalyst | Reaction[d] Time (hrs) | Product[b] | Yields[c] (%) |
|---|---|---|---|---|---|---|
| 1 | 2 | Aniline | 1a | 3.0 | Acetanilide | 98 |
| 2 | 3 | Aniline | 1b | 3.5 | Acetanilide | 98 |
| 3 | 4 | P-nitroaniline | 1b | 3.0 | P-nitroacetanilide | 97 |
| 4 | 5 | m-nitroaniline | 1b | 6.0 | m-nitro acetanilide | 98 |
| 5 | 6 | P-chloroaniline | 1a | 3.0 | P-chloro acetanilide | 99 |
| 6 | 7 | P-chloroaniline | 1b | 4.0 | P-chloro acetanilide | 99 |
| 7 | 8 | P-anisidine | 1a | 2.5 | P-acetanisidine | 99 |
| 8 | 9 | P-anisidine | 1b | 4.5 | P-acetanisidine | 99 |
| 9 | 10 | P-aminophenol | 1a | 3.0 | p-hydroxy acetanilide | 98 |
| 10 | 11 | P-aminophenol | 1b | 3.5 | p-hydroxy acetaaiiide | 98 |
| 11 | 12 | o-aminophenol | 1a | 3.0 | o-hydroxy acetanilide | 99 |
| 12 | 13 | o-aminophenol | 1b | 3.5 | o-hydroxy acetaniiide | 99 |
| 13 | 14 | 4-bromo-2-methyl aniline | 1a | 3.0 | 4-bromo-2-methylacetanilde | 97 |
| 14 | 15 | 4-bromo-2-methyl aniline | 1b | 4.0 | 4-bromo-2-methylacetanilde | 98 |
| 15 | 16 | 4-amino-2-nitro toluene | 1a | 3.0 | 4-acetamido-2-nitrotoluene | 98 |
| 16 | 17 | 4-amino-2-nitro toluene | 1b | 3.5 | 4-acetamido-2-nitrotoluene | 98 |
| 17 | 18 | Benzylamine | 1a | 0.08 | N-(phenylmethyl) acetamide | 98 |
| 18 | 19 | Benzylamine | 1b | 0.2 | N-(phenylmethyl) acetamide | 98 |
| 19 | 20 | Phenethylamine | 1b | 1.0 | N-(2-phenylethyl) acetamide | 99 |

TABLE 1-continued

N-acetylation of amines using acetic acid as acetylating agent

| S. No. | Example | Amine[a] (Substrate) | Catalyst | Reaction[d] Time (hrs) | Product[b] | Yields[c] (%) |
|---|---|---|---|---|---|---|
| 20 | 21 | (D)-(+)-α-methy1 benzylamine | 1a | 0.75 | (D)-(+)-N-(1-phenylethyl) acetamide | 98 |
| 21 | 22 | (D)-(+)-α-methy1 benzylamine | 1b | 1.0 | (D)-(+)-N-(1-phenylethyl) acetamide | 98 |
| 22 | 23 | Furfurylamine | 1a | 2.5 | N-furfuryl acetamide | 97 |
| 23 | 24 | Furfurylamine | 1b | 3.0 | N-furfuryl acetamide | 98 |
| 24 | 25 | 2-(2-aminoethyl) pyridine | 1a | 3.5 | 2-(2-acetamino-ethyl) pyridine | 95 |
| 25 | 26 | 2-(2-aminoethyl) pyridine | 1b | 4.0 | 2-(2-acetamino-ethyl) pyridine | 96 |
| 26 | 27 | Cyclohexylamine | 1a | 3.0 | N-cyclohexyl acetamide | 97 |
| 27 | 28 | Cyclohexylamine | 1b | 3.5 | N-cyc1ohexyl acetamide | 98 |
| 28 | 29 | Propargylamine | 1a | 4.0 | N-propargyl acetamide | 72 |
| 29 | 30 | Propargylamine | 1b | 4.5 | N-propargyl acetamide | 70 |
| 30 | 31 | Dodecylamine | 1a | 3.5 | N-dodecyl acetamide | 98 |
| 31 | 32 | Dodecylamine | 1b | 4.5 | N-dodecyl acetamide | 98 |
| 32 | 33 | 2-methyl-2-amino-l,3-propanediol | 1b | 1.5 | 2-methyl-2-N-acetamido-1,3-propanediacetate | 96 |
| 33 | 34 | 1-naphthylamine | 1a | 5.0 | N-1-naphthyl acetamide | 99 |
| 34 | 35 | l-naphthylamine | 1b | 6.0 | N-1-naphthyl acetamide | 99 |

1a: catalyst, which is described in write-up as Example 1a
1b: catalyst, which is described in write-up as Example 1b
a: amine & acetic acid molar ratio was 1:10
b: all products were identified by their $^1$H NMR and mass spectroscopy and/or comparison of their b.p or m.p with authentic samples.
c: isolated yields.
d: where acetic acid reflux temperature was maintained.

It was found that the Fe3+-montmorillonite and natural montmorillonite clays were found to be the efficient catalysts for the exclusive formation of amides from various amines in presence of acetic acid. The natural montmorillonite's activity is comparable with $Fe^{3+}$-exchanged K10 montmorillonite.

TABLE 2

N-acetylation of amine using propionic acid as acetylating agent

| S. No. | Example | Amine[a] Substrate | Catalyst | Reaction[b] Time (hrs) | Product[c] | Yields[d] (%) |
|---|---|---|---|---|---|---|
| 35 | 36 | (D)-(+)-α-methyl benzylamine | 1a | 1.0 | (D)-(+)-N-(1-phenylethyl) propanamide | 99 |
| 36 | 37 | (D)-(+)α-methy1 benzylamine | 1b | 1.2 | (D)-(+)-N-(1-phenylethyl) propanamide | 99 |

1a: catalyst, which is described in write-up as Example 1a
1b: catalyst, which is described in write-up as Example lb
a: amine and propionic acid molar ratio was 1:10
b: where propionic acid reflux temperature was maintained
c: all products were identified by their $^1$H NMR and mass spectroscopy and/or comparison of their b.p. or m.p. with authentic samples.
d: isolated yields.

The main advantages of the present invention are:
1. The present process completely eliminates the use of expensive acetic anhydride as an acetylating agent.
2. Carboxylic acid such as acetic acid, propionic acid, butyric acid etc., are used as the acylating agents in place of the corresponding anhydrides for the acylation of various substrates (aliphatic, aromatic, cyclic and heterocyclic amines) for the first time.
3. Clays have been used as catalysts for the acetylation of various amines for the first time in place of expensive homogeneous catalysts necessitating typical and laborious work up.
4. An ecofriendly and very simple process for the production of amides was developed.
5. The selectivity and yields obtained in this process are quantitative.
6. The reactions are simple, facilitated at lower temperatures with shorter durations. Workup procedure is easy.
7. The support of the catalyst/catalyst is cheap and abundantly available in nature.
8. The present process envisages no disposal problem as the catalyst can be used for several cycles. The catalyst was subjected to four cycles, which displayed consistent activity.
9. The present process is environmentally safe since there is no effluent disposal problem.
10. The process is economical.

We claim:
1. A single step process for preparing an amide which comprises reacting an amine having from 1 to 20 carbon atoms an selected form the group consisting of aromatic, aliphatic, carbocyclic and heterocyclic amines with an acylating agent consisting essentially of a carboxylic acid selected from the group consisting of acetic, propionic and butyric acids in a molar ratio of acid to amine of from 3:1 to 10:1 in the presence of reusable natural montmorillionite or a metal ion exchanged montmorillionite clay catalyst in a suitable solvent medium at a temperature in the range 30–160° C. for from 0.02 to 6 hours and recovering the corresponding amides.

2. A process as claimed in claim 1 wherein the clay catalyst used is metal-ion exchanged montmorillonite selected from the group consisting of $Fe^{3+}$, $Co^{2+}$, $Cu^{2+}$, $Zn^{2+}$, $Al^{3+}$, $Ce^{3+}$, $La^{3+}$ and $Zr^{4+}$-montmorillonites.

3. A process as claimed in claim 1 wherein the carboxylic acid is used in an amount in the range of 3 to 10 mmoles/mmole of amine.

4. A process as claimed in claim 2 wherein the said amines are selected from the group consisting of p-aminophenol; o-aminophenol; p-nitroaniline; m-nitroaniline; p-chloroaniline; aniline (amino benzene); benzylamine; phenylethylamine; p-anisidine; (D)-(+)-α-methylbenzylamine; 4-bromo-2-methylaniline; 4-amino-2-nitrotoluene; 2-(2-amino ethyl)pyridine; furfurylamine; 2-methyl-2-amino-1, 3-propanediol; dodecylamine; propargyl amine; cyclohexylamine and 1-naphthylamine.

5. A process as claimed in claim 1 wherein said solvent is selected from the group consisting of dichloroethane, toluene, chlorobenzene and acetic acid.

6. A process as claimed in claim 1 wherein the recovery of amides is carried out by separating the catalyst through filtration and removing the solvent by rotavapor or distillation.

7. A process as claimed in claim 1 wherein the unreacted carboxylic acid acylating agent is recovered by distillation and recycled to the reaction system.

8. A single step process for the preparation of amide which comprises reacting an amine having 1 to 20 carbon atoms selected from the group consisting of aromatic, aliphatic, cyclic and heterocyclic amines with a carboxylic acid selected from acetic acid, propionic acid and butyric acid in a molar ratio of 1:3 to 1:10 in the presence of a reusable metal-ion exchanged montmorillonite catalyst selected from $Fe^{3+}$, $Co^{2+}$, $Cu^{2+}$, $Zn^{2+}$, $Al^{3+}$, $Ce^{3+}$, $La^{3+}$ and $Zr^{4+}$-montmorillonite catalysts, in a suitable solvent medium at a temperature in the range of 30–160° C. for a period of 0.02 to 6 hours, and recovering the corresponding amides by a conventional simple work-up procedure.

9. A process as claimed in claim 8 wherein the amount of said carboxylic acid is in the range of 3 to 10 mmoles per mmole of substrate.

\* \* \* \* \*